Figure 1:
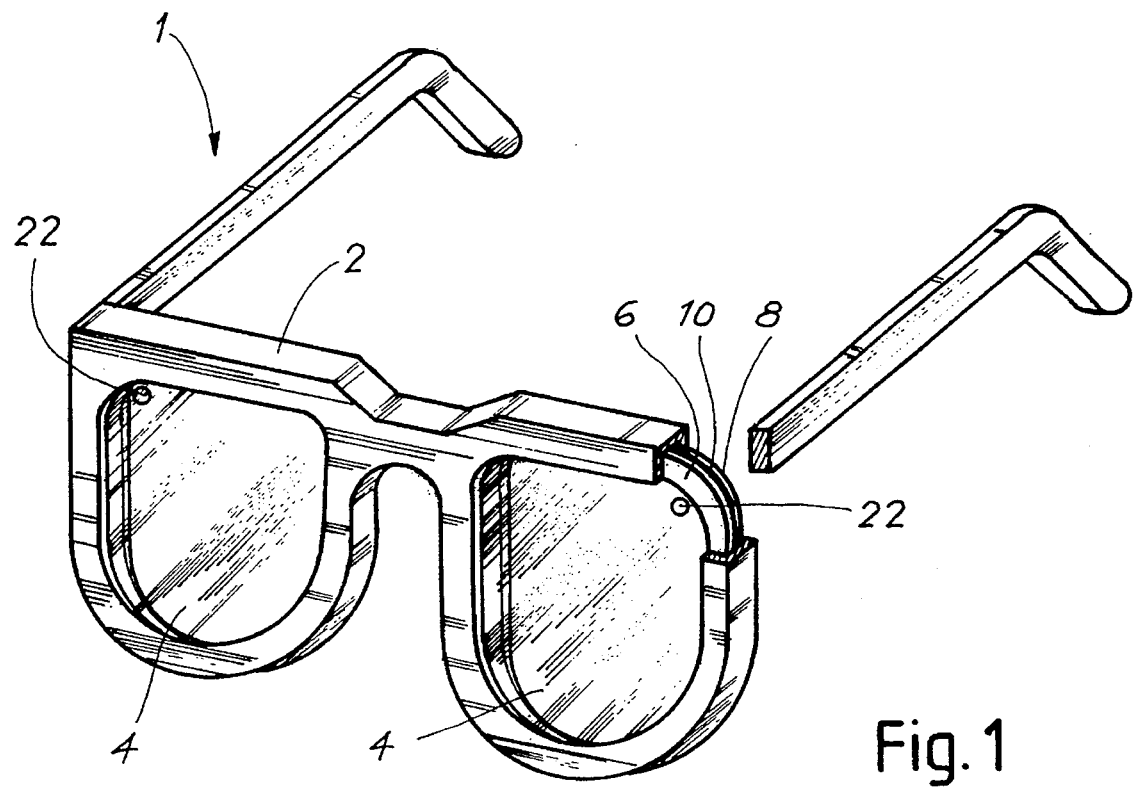

United States Patent
Grupp

Patent Number: 5,608,567
Date of Patent: Mar. 4, 1997

[54] VARIABLE TRANSPARENCY ELECTRO-OPTICAL DEVICE

[75] Inventor: Joachim Grupp, Neuchâtel, Switzerland

[73] Assignee: Asulab S.A., Bienne, Switzerland

[21] Appl. No.: 500,642

[22] Filed: Jul. 11, 1995

Related U.S. Application Data

[63] Continuation of Ser. No. 84,223, Jul. 5, 1993, abandoned.

[30] Foreign Application Priority Data

Nov. 5, 1991 [CH] Switzerland .......................... 03218/91
Dec. 17, 1991 [FR] France .................................. 91 15768

[51] Int. Cl.⁶ .............................. G02F 1/153; G02C 7/10
[52] U.S. Cl. .......................... 359/275; 359/265; 359/272; 359/245; 359/614; 359/722; 359/738; 359/13; 359/104; 351/44
[58] Field of Search .................................. 359/36, 48, 40, 359/49, 53, 55, 62, 66, 72, 74, 77, 80, 90, 94, 96, 98, 103, 106, 490, 491, 611, 614, 722, 738, 265, 266, 272, 273, 274, 275, 245; 351/44

[56] References Cited

U.S. PATENT DOCUMENTS

| | | | |
|---|---|---|---|
| 4,756,605 | 7/1988 | Okada et al. ......................... | 351/44 X |
| 4,968,127 | 11/1990 | Russell et al. ......................... | 351/44 |
| 4,986,639 | 1/1991 | Chang et al. ......................... | 359/77 X |
| 5,015,086 | 5/1991 | Okaue et al. ......................... | 351/44 |
| 5,114,218 | 5/1992 | Black et al. ......................... | 351/44 |
| 5,128,799 | 7/1992 | Byker ......................... | 359/265 |
| 5,172,256 | 12/1992 | Sethofer et al. ......................... | 359/77 |
| 5,184,156 | 2/1993 | Black et al. ......................... | 351/44 X |
| 5,382,986 | 1/1995 | Black et al. ......................... | 351/44 X |
| 5,412,439 | 5/1995 | Horn ......................... | 351/45 |
| 5,455,638 | 10/1995 | Kallman et al. ......................... | 351/44 |
| 5,552,841 | 9/1996 | Gallorini et al. ......................... | 351/49 |

FOREIGN PATENT DOCUMENTS

| | | | |
|---|---|---|---|
| 0091514 | 10/1983 | European Pat. Off. ............. | 359/77 X |
| 0157744 | 10/1985 | European Pat. Off. ............. | 359/77 X |
| 2293188 | 12/1975 | France ......................... | 359/77 X |
| 2416519 | 8/1979 | France ......................... | 359/77 X |
| 2169417 | 7/1986 | United Kingdom ................. | 359/77 X |
| WO87/06018 | 10/1987 | WIPO ......................... | 359/77 X |

*Primary Examiner*—Brian Healy

[57] ABSTRACT

The invention relates to a variable transparency electro-optical device comprising: at least one lens formed by an electro-optical cell (4) comprising a first plate (6) and a second plate (8) each provided with a control electrode (14, 16) and a sealing frame (10) interposed between the two plates to form a sealed volume enclosing an electro-optical material (12), voltage generating means (18) connected to said electrodes to apply a variable voltage to said material in order to automatically or manually vary the transmission of the cell (4) as a function of the ambient light. According to the invention the cell (4) comprises at least one element (6) charged with a photochromic substance having an absorption that varies in reversible manner as a function of the intensity of the light impinging on said cell. The invention has particular applications in devices for protecting the eyes.

13 Claims, 1 Drawing Sheet

VARIABLE TRANSPARENCY ELECTRO-OPTICAL DEVICE

This is a continuation of application Ser. No. 08/084,223, filed on Jul. 5, 1993, now abandoned.

The invention relates to a variable transparency electro-optical device and more particularly to a device of this type applied to devices for protecting the eyes such as glasses comprising lenses composed of electro-optical cells which possess particularly high light absorption characteristics.

The field of application of the invention also comprises conventional sun glasses or medical glasses, as well as devices for protecting the eyes, such as welding goggles or the like.

Variable transparency glasses are currently known and are used notably as sun glasses and are of two types.

The first type comprises glasses provided with lenses termed photochromic lenses. These latter include a photochromic substance such as a silver salt and have the property of passing, automatically and reversibly, from an almost transparent state in the absence of sunlight to an absorbent state in the presence of sunlight.

By virtue of their nature, these glasses generally only permit absorption of a maximum amount of light of the order of 70 to 80% of the ambient light and then only after a reaction time of about ten minutes.

Moreover the regeneration time after the lenses are no longer irradiated is about 10 to 20 minutes and the transmission of these lenses in the transparent state is only about 80%, these lenses permanently retaining a slightly coloured appearance.

In addition, these glasses are virtually ineffective when used behind a glass surface since these polychromic lenses are substantially sensitive to ultraviolet light. These lenses are also very sensitive to temperature and will be more absorbent at low temperature than at high temperature to a similar quantity of ambient light.

Finally, it is difficult, for the same degree of absorption, to provide glasses of this kind having lenses less than several mm in thickness without the risk of reaching the limit of solubility of the photochromic substances and thus without the risk of causing the precipitation thereof.

This results in glasses which react passively and which are only relatively user-friendly if it is desired to obtain sun glasses that react immediately and efficiently in a large number of situations and notably behind a glass surface such as a windscreen of a motor vehicle.

The second type comprises glasses, the lenses of which are formed of electro-optical cells such as liquid crystal cells, such as the glasses described in the patent specification NO. PCT/IT87/00024.

This document relates to positive contrast liquid crystal cells of the dichroic type associated with an automatic or manual control circuit which makes it possible to change the cells from a transparent state to an absorbent state. In the transparent state, these cells transmit about 80% of the ambient light whereas they transmit about 40% in the absorbent state. Although these glasses constitute a major advantage over photochromic glasses because they are active and their reaction time is virtually zero after the control circuit has been activated, it notably being possible to activate the latter by ambient light detection means or by a simple cut-out switch, they still present some disadvantages.

These glasses have on the one hand a rather low coefficient of absorption with the result that the user is poorly protected in the present of strong light and may be inconvenienced. On the other hand, the plates of these cells have to be subjected to an anti-ultraviolet treatment to prevent premature degradation of the liquid crystal which, apart from the fact that it is costly, gives a yellowish and not very aesthetic appearance to the plates of the cells in their transparent state.

It is thus a main object of the invention to overcome the disadvantages of the above-mentioned prior art by providing a variable transparency electro-optical device which combines the advantageous features of the use of photochromic cells and of electro-optical cells.

The object of the invention is thus a variable transparency electro-optical device comprising:

at least one lens composed of an electro-optical cell comprising a first plate and a second plate each provided with a control electrode and a sealing frame interposed between the two plates to form a sealed volume enclosing an electro-optical material, voltage generating means connected to said electrodes to apply a variable voltage to said material in order to vary the transmission of the cell automatically or manually as a function of the ambient light, this device being characterized in that the cell comprises at least one element charged with a photochromic substance having a transmission which varies in reversible manner as a function of the intensity of the light impinging on said cell.

These characteristics make it possible to produce a variable transparency electro-optical device having two successive absorption levels with two different reaction speeds which permit immediate and effective reaction to every light source and which, in addition, have a high coefficient of absorption to ambient light.

It will also be noted that the element charged with a photochromic substance advantageously forms a screen against ultraviolet radiation so that the electro-optical material is protected thereagainst.

In addition, dividing the absorption of the ambient light between the electro-optical material and an element charged with a photochromic substance makes it possible for the latter to be charged either with a lesser amount of said substance than that normally needed or to provide lenses of very low thickness which advantageously reduces the weight of the entire device.

It will be noted that especially in the application of a device of this kind to means for protecting the eyes such as glasses, the absorptive effect of the electro-optical cells and the photochromic effect are complementary in numerous common situations. Thus for example, in a motor vehicle in which the absorption of the photochromic lenses is almost zero whereas that of the electro-optical cells is normally effective. Moreover, when the wearer passes outdoors from a sunny area to a partially shaded area in which he wishes to be protected, the electro-optical cells are easily deactivated, the wearer then only benefiting from the absorptive effect of the photochromic lenses.

According to a preferred embodiment, the element charged with a photochromic substance is formed by one of the plates of the electro-optical cell.

It is also an object of the invention to provide a device of this type disposed in a supporting structure to form therewith a device for protecting the eyes.

Figure 2:
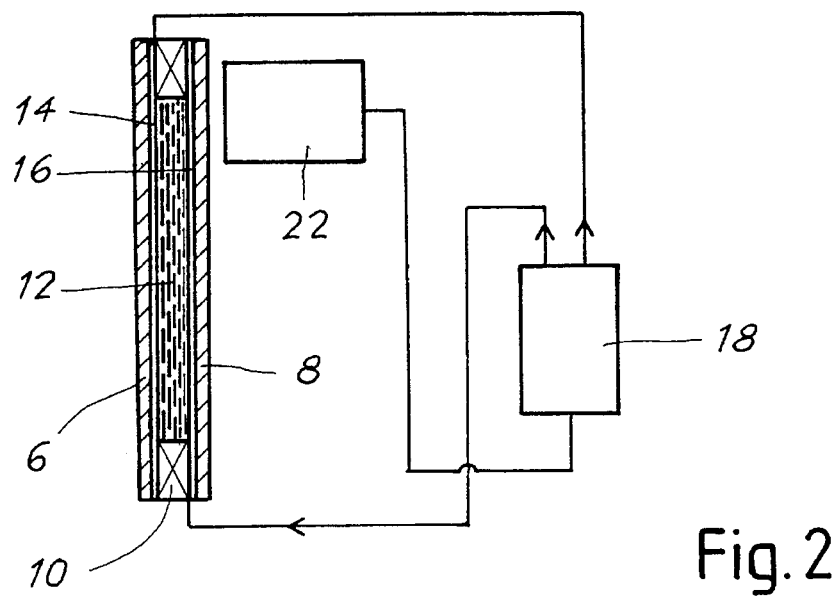

Other advantages and features of the invention will emerge from study of the following detailed description of embodiments of the invention, given as non-limiting example, in connection with the appended drawings, in which:

FIG. 1 is a partially exploded perspective view of an electro-optical device of the invention applied to a pair of glasses; and FIG. 2 is a diagrammatic section of an electro-optical device of the invention associated with an automatic circuit for controlling its transparency, equipping the glasses of FIG. 1.

The following description of the electro-optical device according to the invention will be made in the context of its application in variable transparency glasses, but it is understood that a device of this kind can have other interesting applications, for example in welding goggles or the like or also to produce glass for windows.

Whereas the electro-optical material used in the cell of the device of the invention described hereinafter is a mixture of liquid crystals, other types of electro-optical materials such as notably electrochromic materials may of course also be used.

FIG. 1 shows a pair of variable transparency liquid crystal glasses according to the invention and having the general reference 1. These glasses are generally designed to protect the sight of their wearer against ambient light of strong intensity. More specifically, these glasses comprise a frame 2 into which are fitted in conventional manner lenses 4, the absorption characteristics of which vary reversibly as a function of the intensity of the light impinging on the lenses.

These lenses 4 are formed of liquid crystal cells which, as may be seen in particular from FIG. 2, each comprise a transparent front plate 6 and a transparent back plate 8 connected together by a sealing frame 10. These two plates 6, 8 and the frame 10 define a sealed volume enclosing a mixture 12 of liquid crystals and dichroic dyestuffs doped with a chiral agent.

In the embodiment described the plates 6 and 8 are convex and each have on their inside face a transparent electrode 14, 16 covered by an alignment layer (not shown) which extends over the entirety of each plate. The electrodes 14, 16 are composed for example of a mixture of indium oxides and tin oxides and the alignment layer is formed of silicon dioxide with a surfactant agent of the octadecyltrialkoxysilane type fixed thereto.

It should be noted that the drawings do not represent the exact thickness of the assembly formed in this manner, this thickness being greatly exaggerated for sake of clarity. More specifically, the distance between the two electrodes is of the order of 5 to 9 μm.

FIG. 2 also shows that the cells 4 are associated with an electrical control circuit 18 fed for example by a battery or by solar cells integrated in the frame 2 (not shown). This circuit is connected to ambient light detection means 22 formed by one or several photosensitive sensors which deliver an electrical control signal representing the intensity of light which they receive. This circuit also comprises two outputs connected to electrodes 14 and 16 respectively in order to control the degree of absorption of the cells.

In other words, the signal produced by the control circuit 18 is applied to the electrodes of the cells to vary the electrical field applied to the mixture 12 which they contain. The effect of this variation is to modify the transmission of the cell which results in variation in its degree of light absorption.

In the embodiment shown, the electro-optical cells 4 and the sensor 22 are disposed in relation to one another in such a way that incident light or ambient light reaches said cells first. An arrangement of this type of the sensor or sensors notably makes it possible, as will be explained below, to obtain constant transmission in a range of the level of light. It goes without saying that in a different embodiment the detection means can be disposed so as to be directly irradiated by the light rays which the device of the invention is designed to absorb.

According to the invention each cell comprises at least one element charged with a photochromic substance, said element being disposed on the cell in such a manner that the ambient light reaches this element first when the glasses are worn by a user.

In the example described, said element is formed by the plate 6 of the cell 4. This plate is charged with a photochromic substance such as a silver salt and can be either a glass plate or of a synthetic material with optical properties equivalent to those of the glass. A plate of synthetic material made of polyvinyl pyrolidine doped with microcrystals of AgCl is perfectly suitable. This plate of synthetic material can also be made using films of laminated polyester on a synthetic plate, for example a plate sold under the reference CR 39 by ESSILOR, by means of an adhesive doped with polychromic spirooxazines.

The concentration of photochromic substance should preferably not exceed 3% by weight and the thickness of said element 6 is of the order of 1 mm.

In another embodiment of the invention, not shown, said element can be formed of a supplementary plate directly applied to the plate 6 of the cells, for example by adhesion.

According to another embodiment (not shown) of the invention, the lenses 4 formed by an electro-optical cell can be associated with a second electro-optical cell in the same support structure to reinforce the absorptive effect of the device for protecting the eyes such as welding goggles. In this case the second cell is placed behind the lenses 4 in relation to the ambient light and this cell can be an electro-optical cell of conventional variable transparency.

The applicant has conducted comparative measurements of the transmission (in % of light received) of a single electro-optical cell in a switched and a non-switched state, of a single photochromic lens and of the electro-optical device of the invention in a switched and non-switched state in the presence of and in the absence of light comprising UV radiation for purposes of illustration and to better demonstrate the advantageous results of combining the photochromic and electro-optical effects of the invention.

The measurements in the presence of light were made in the presence of a light source of 40 mW/cm$^2$. The electro-optical cell used is a liquid crystal cell comprising a dichroic mixture sold by MERCK under reference ZLI 4282, this mixture being doped with 0.85% by weight of a chiral agent sold by MERCK under reference S811.

The substrates of this cell are of glass. The photochromic lenses used are standard photochromic lenses which can for example be obtained from Desag (Schott). It will also be noted that the results of the transmission measurements of the device of the invention were obtained with a device in which the charged element of a photochromic substance is applied to the electro-optical cell by adhesion.

The results obtained are set out in the following table:

|  | TRANSMISSION (%) | |
| --- | --- | --- |
|  | without light | with light |
| Photochromic lenses | 75 to 85% | 20 to 30% |
| Electro-optical cell | | |
| - non-switched | 80% | |
| - switched | 40% | |
| Electro-optical device of the invention | | |
| - non-switched | 70% | 19% |
| - switched | 27% | 9% |

This table shows that the device of the invention presents a degree of absorption that can vary over a large range as a function of the intensity of the ambient light.

In other words, the device of the invention can become very absorbent in the event of great luminosity and only transmit 9% of the ambient light compared to 20 and 40% with a photochromic lens alone and respectively a variable transparency electro-optical cell alone (in its switched state).

The device of the invention can also become very transmissive in the event of total interruption of the luminosity and transmit 70% of the ambient light (in the switched state of the electro-optical cell). Such a level of transmission is substantially equal to the level of transmission of the photochromic lenses and electro-optical cells used on their own.

If the electro-optical device of the invention is interposed between detection means 22 and the light source, the transparency of the device can regulate itself so as to be substantially constant for periods of transition notably corresponding to the transition of a dark or poorly luminous medium to a clear or luminous medium.

During transition of this type, the detection means initially receive almost all the light in such a way that they immediately control the darkening of the electro-optical cell when the photochromic substance has not yet reacted. The wearer thus has immediate protection.

In a second phase, that is a few minutes later, the photochromic element, for example the photochromic substrate of the cell, begins to react progressively and in turn absorbs part of the ambient light. The illumination of the detection means situated behind the cell is then diminished while the latter trigger a control signal which increases the transmission of the cell while the photochromic element darkens.

It is thus possible to maintain a degree of constant transmission of the device of the invention both during the transition of a dark medium to a luminous medium and during slight variations in the luminosity of the medium.

In the opposite situation, i.e. in the case of transition from a luminous medium towards a darker medium, the cell deactivates immediately with the result that the device rapidly becomes less absorbent, the photochromic element then progressively loses its ability to absorb until it reaches a completely clear or sufficiently clear state for the device to be able to readjust itself once again as has been described above.

I claim:

1. A variable transparency electro-optical device comprising:

at least one lens formed by an electro-optical cell comprising a first plate and a second plate each provided with a control electrode and a sealing frame interposed between the two plates to form a sealed volume;

an electro-optical material filling said sealed volume; and, voltage generating means connected to said electrodes to apply a variable voltage to said material in order to automatically or manually vary the transmission of the cell as a function of the ambient light, wherein the cell comprises at least one element other than said electro-optical material charged with a photochromic substance having an absorption that varies in reversible manner as a function of the intensity of the light impinging on said cell.

2. A device according to claim 1, wherein said element is formed by one of the plates of said cell.

3. A device according to claim 1, wherein it comprises two elements formed by the first and second plate respectively of said cell.

4. A device according to claim 1, wherein said element is formed by an additional layer directly applied to a plate of said cell.

5. A device according to claim 1 wherein said electro-optical material is a mixture of dichroic liquid crystals and dichroic dyestuffs.

6. A device according to claim 5, wherein said mixture of liquid crystals is doped with a chiral agent.

7. A device according to claim 1 wherein said electro-optical material is an electrochromic material.

8. A device according to claim 1 wherein said plates are made of a synthetic material.

9. A device according to claim 1 wherein it also comprises detection means capable of delivering a control signal dependant on the intensity of the light impinging on these detection means, said voltage generating means acting on the transparency of the cell in response to said control signal.

10. A device according to claim 9, wherein the electro-optical cell and said detection means are disposed in relation to one another in such a manner that ambient light sensed by said detection means reaches said detection means after passing through said cell.

11. A device for protecting the eyes comprising a support structure in which is mounted a variable transparency electro-optical device, wherein said electro-optical device is according to claim 1.

12. A device for protecting the eyes according to claim 11, wherein it also comprises a second electro-optical cell mounted in said support structure.

13. A device for protecting the eyes according to claim 11 wherein the voltage generating means are composed of solar cells.

* * * * *